US006916831B2

(12) United States Patent
Lee et al.

(10) Patent No.: US 6,916,831 B2
(45) Date of Patent: Jul. 12, 2005

(54) FLAVONE ACETIC ACID ANALOGS AND METHODS OF USE THEREOF

(75) Inventors: Kuo-Hsiung Lee, Chapel Hill, NC (US); Yi Xia, Foster City, CA (US); Zheng-Yu Yang, Foster City, CA (US); Kenneth F. Bastow, Chapel Hill, NC (US); Sheng-Chu Kuo, Tai Chung (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/373,399

(22) Filed: Feb. 24, 2003

(65) Prior Publication Data

US 2004/0167151 A1 Aug. 26, 2004

(51) Int. Cl.[7] ................ A61K 31/445; A61K 31/35; C07D 211/06; C07D 257/04; C07D 311/82
(52) U.S. Cl. ................ 514/320; 514/422; 514/382; 514/432; 514/460; 514/451; 514/252; 546/202; 546/196; 548/253; 548/527; 548/517; 549/5; 549/23; 549/218; 549/399; 549/400; 549/403
(58) Field of Search ................ 549/400, 403, 549/218, 399, 5, 23; 514/252, 320, 382, 422, 432, 460, 451; 548/253, 527, 517; 546/202, 196

(56) References Cited

U.S. PATENT DOCUMENTS

| 5,399,584 A | * 3/1995 | Ares et al. ............. 514/432 |
| 5,403,842 A | * 4/1995 | Leonardi et al. ....... 514/252.13 |
| 5,571,822 A | 11/1996 | Lee et al. |
| 5,733,920 A | 3/1998 | Mansuri et al. |
| 5,994,367 A | 11/1999 | Lee et al. |

FOREIGN PATENT DOCUMENTS

| JP | 2004043457 | * 2/2004 |
| WO | WO 2002009700 | * 2/2002 |
| WO | WO 02/26730 A2 | 4/2002 |

OTHER PUBLICATIONS

Kanwar, Cancer Research, Vol 61, pp 1648–1956, 2001.*
Sheng–Chu Kuo et al., *Synthesis and Cytoxicity of 1,6,7, 8–Substituted 2–(4'–Substituted phenyl)–4–quinolones and Related Compounds: Identification as Antimitotic Agents Interacting with Tubulin*, J. Med. Chem, 1993, 1146–1156.
Leping Li, et al., *Antitumor Agents. 150. 2,3,4,5,5,6,7–Substituted 2–Phenyl–4–quinolones and Related Compounds: Their Synthesis, Cytotoxicity, and Inhibition of Tubulin Polymerization*, J. Med. Chem, 1994, 37:1126–1136.

Li et al., "Antitumor Agents 150. 2',3;,4',5',5',6,7–Substituted 2–Phenyl–4–quinolones and Related Compounds: Their Synthesis, Crytoxicity, and Inhibition of Tubulin Polymerization" *J. Med. Chem.* 37 1126–1135 (1994).

Xia et al.; "Antitumor Agents. 181. Synthesis and Biological Evaluation of 6,7,2',3',4'–Substituted–1,2,3, 4–tetrahydro–2–phenyl–4–quinolones as a New Class of Antimitotic Antitumor Agents" *J. Med. Chem.* 41 1155–1162 (1998).

Xia et al.; "Antitumor Agents. 211. Fluorinated 2–Phenyl–4–quinolone Derivatives as Antimitotic Antitumor Agents[1]" *J. Med. Chem.* 44 3932–3936 (2001).

* cited by examiner

*Primary Examiner*—D. Margaret Seaman
(74) *Attorney, Agent, or Firm*—Myers Bigel Sibley & Sajovec, P.A.

(57) ABSTRACT

Compounds are described having a structure according to Formula I or Formula II:

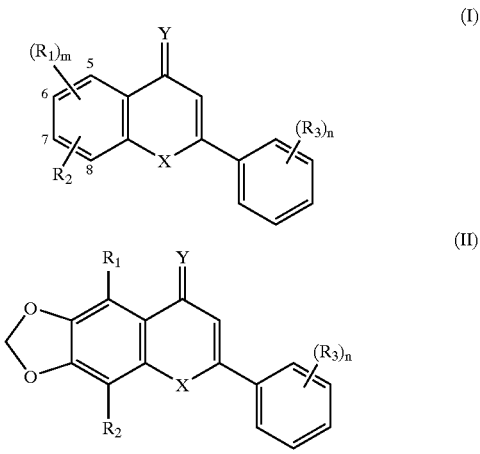

wherein: X is selected from the group consisting of O, NH, and S; Y is selected from the group consisting of O and S; m is from 1 to 3; n is from 1 to 5; $R_1$ and $R_3$ are each independently selected from the group consisting of H, hydroxy, lower alky, lower alkoxy, halo, amino, aminoalkyl, nitro, heteroaryl, —OC(=O)$R_6$, —O(C=O)O$R_6$; and —O(C=O)N($R_6$)$_2$; and $R_2$ is side chain such as an acetic acid side chain, where p is 0 to 4, $R_5$ is hydroxy, alkoxy or amino, and $R_6$ is H or lower alkyl, or a pharmaceutically acceptable salt thereof. The compounds are useful for the treatment of cancer.

19 Claims, No Drawings

FLAVONE ACETIC ACID ANALOGS AND METHODS OF USE THEREOF

STATEMENT OF FEDERAL SUPPORT

This invention was made with government support under grant number CA-17625 from the National Institutes of Health. The U.S. Government has certain rights to this invention.

FIELD OF THE INVENTION

This invention relates to compounds, pharmaceutical formulations and methods of use thereof for medical purposes such as the treatment of cancer.

BACKGROUND OF THE INVENTION

Flavone acetic acid (FAA, Scheme 1) is a synthetic flavone with a unique pattern of antitumor activity.

Scheme 1

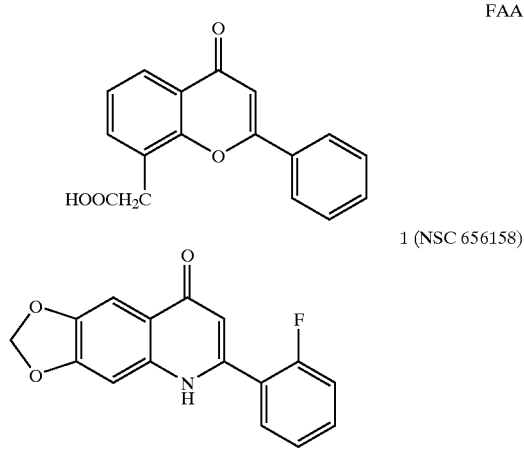

Unlike conventional antitumor agents, it causes rapid tumor necrosis with little resultant toxicity in normal tissues. FAA has demonstrated excellent activity against marine colon adenocarcinoma 38 and a broad spectrum of slow-growing solid tumors that are usually insensitive to most cytotoxic drugs (J. Plowman, et al., *Cancer Treatment Reports* 1986, 70, 631; G. Atassi et al., *Eur. J. Med. Chem. Chim. Ther.* 1995, 20, 393). In contrast to its solid tumor activity, FAA shows poor activity against murine leukemia cell lines (P388 and L1210). Because of its unique preclinical solid tumor activity, FAA has been evaluated in clinical trials (M. Bibby and J. Double, *J. A. Anti-Cancer Drugs* 1993, 4, 3). FAA's precise mechanism of anticancer action in experimental animals is poorly understood (S. Harris, et al., *Biochem. & Biophy. Res. Commun..* 1997, 235, 509; J. Murray et al., *Eur. J. Cancer.* 1991, 27, 765), but undoubtedly is novel. Modification of FAA is continuing (P. Valenti et al., *Anti-Cancer Drug Design.* 1996, 11, 243).

In previous studies, numerous substituted 2-phenyl-4-quinolones were synthesized and evaluated for antimitotic and antitumor activities. Most compounds in this series showed promising in vitro activity in the NCI's human tumor cell lines (HTCL) assay with $GI_{50}$ values in the low micromolar to nanomolar concentration range. In general, a good correlation was found between cytotoxicity and inhibition of tubulin polymerization (S. Kuo et al., *J. Med. Chem.* 1993, 36, 1146; L. Li et al., *J. Med. Chem.* 1994, 37, 3400; L. Li et al., *J. Med. Chem.* 1994, 37, 1126; Y. Xia et al., *J. Med. Chem.* 1998, 41, 1155). Thirteen compounds in this series have been selected for in vivo xenograft testing, and to date, compound 1 (NSC 656158) is active in vivo. In the xenograft ovarian OVCAR-3 model, treated mice demonstrated a 130% increase in life span.

SUMMARY OF THE INVENTION

A first aspect of the present invention is a compound having a structure according to Formula I or Formula II:

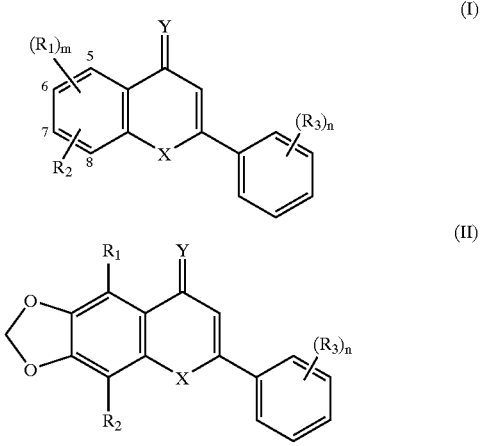

wherein:
X is selected from the group consisting of O, NH, and S;
Y is selected from the group consisting of O and S;
m is from 1 to 3;
n is from 1 to 5;
$R_1$ and $R_3$ are each independently selected from the group consisting of H, hydroxy, lower alkyl, lower alkoxy, halo, amino, aminoalkyl, nitro, heteroaryl, $-OC(=O)R_6$, $-O(C=O)OR_6$; and $-O(C=O)N(R_6)_2$;
$R_2$ is selected from the group consisting of:

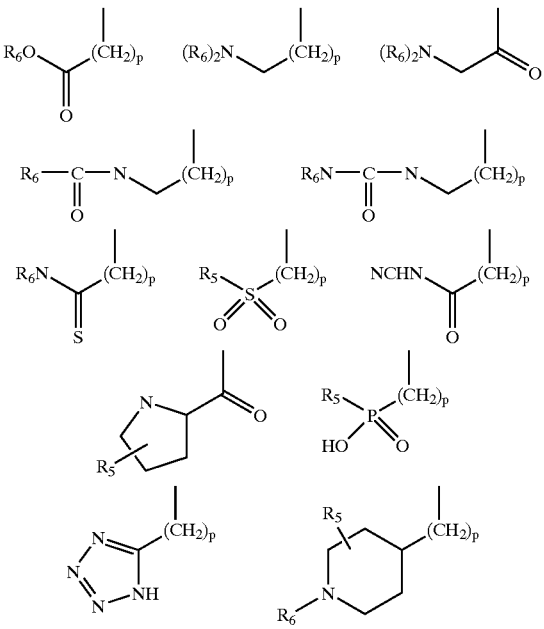

where p is 0 to 4, $R_5$ is hydroxy, alkoxy or amino, and $R_6$ is H or lower alkyl;
or a pharmaceutically acceptable salt thereof.

A further aspect of the present invention is a pharmaceutical formulation comprising a compound as described above in a pharmaceutically acceptable carrier, such as an aqueous carrier.

A still further aspect of the present invention is a method of treating a cancer, comprising administering to a subject in need thereof a treatment effective amount of a compound as described above, or a pharmaceutically acceptable salt thereof. Suitable cancers that may be treated by such methods include but are not limited to skin cancer, lung cancer, Kaposi's sarcoma, testicular cancer, lymphoma, leukemia, esophageal cancer, stomach cancer, colon cancer, breast cancer, endometrial cancer, ovarian cancer, central nervous system cancer, liver cancer and prostate cancer.

A still further aspect of the present invention is the use of an active compound as described above for the preparation of a medicament for the treatment of cancer.

DETAILED DESCRIPTION OF THE INVENTION

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "lower alkyl" as used herein refers to C1 to C4, C6 or C8 alkyl, which may be linear or branched and saturated or unsaturated.

"Alkenyl" or "lower alkenyl" as used herein likewise refers to C1 to C4 alkenyl, and alkoxy or loweralkoxy as used herein likewise refers to C1 to C4 alkoxy. "Alkoxy" as used herein refers to linear or branched, saturated or unsaturated oxo-hydrocarbon chains, containing a C1 to C4 or C1 to C8 alkyl, including for example methoxy, ethoxy, propoxy, isopropoxy, butoxy, and t-butoxy.

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "alkylenedioxy" refers to a group of the general formula —OR'O—, —OR'OR'—, or —R'OR'OR'— where each R' is independently alkyl.

The term "heteroaryl" used herein refers to a 5- or 6-membered aromatic ring which includes 1, 2, 3 or 4 hetero atoms such as nitrogen, oxygen or sulfur, and Such rings fused to an aryl, cycloalkyl, heteroaryl or cycloheteroalkyl ring (e.g., to provide a C1–C13 heteroaryl). Examples include but are not limited to pyridyl, pyrazolyl, thiophenyl, chromenyl, benzoxazolyl, benzthiadiazolyl, quinazolinyl, quinolinyl, isoquinolinyl and tetrahydroquinolinyl, benzothiophenyl, indolyl, and the like. The heteroaryl groups may be unsubstituted or substituted with optionally include 1 to 4 substituents such as independently selected substituents from those other than "heteroaryl" identified with respect to the group R$_1$ herein.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals, avians) for veterinary purposes. Mammals (including but not limited to dogs, cats, rabbits, horses, etc.) are preferred, with humans being particularly preferred.

A. Active Compounds.

As noted above, the present invention provides compounds (sometimes referred to herein as "active compounds") having a structure according to Formula I or Formula II:

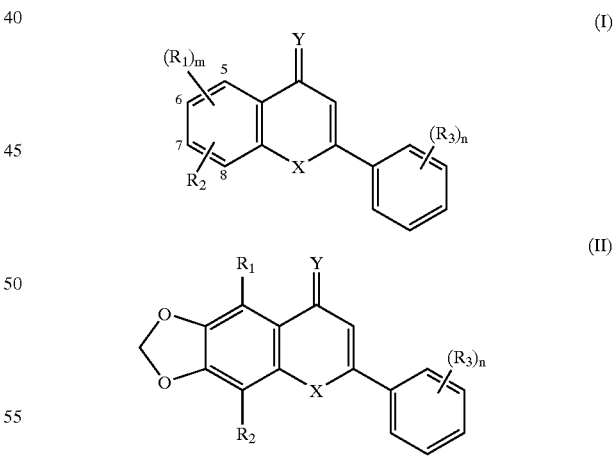

wherein:
X is selected from the group consisting of O, NH, and S;
Y is selected from the group consisting of O and S;
m is from 1 to 3;
n is from 1 to 5;
R$_1$ and R$_3$ are each independently selected from the group consisting of H, hydroxy, lower alkyl, lower alkoxy, halo, amino, aminoalkyl, nitro, heteroaryl, —OC(=O)R$_6$, —O(C=O)OR$_6$; and —O(C=O)N(R$_6$)$_2$;

$R_2$ is selected from the group consisting of:

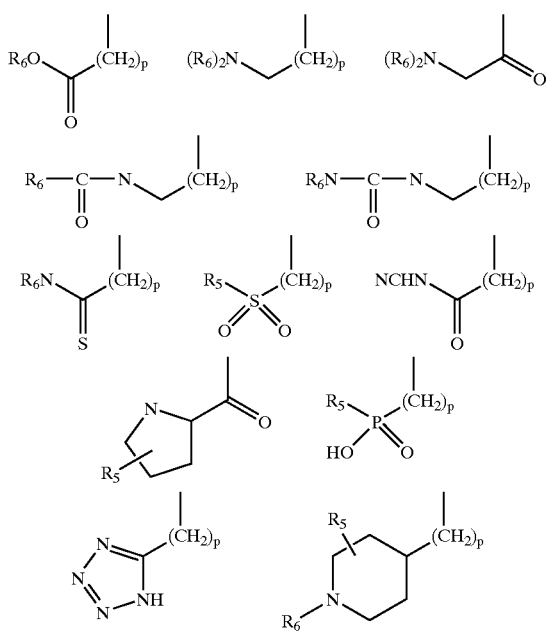
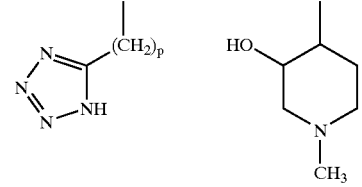

where p is 0 to 4, $R_5$ is hydroxy, alkoxy or amino, and $R_6$ is H or lower alkyl;

or a pharmaceutically acceptable salt thereof.

In some preferred embodiments of compounds of Formula I, $R_2$ is bonded at the 8 position.

In some preferred embodiments of compounds as described above, X is O. In other preferred embodiments of compounds as described above, X is NH. In still other preferred embodiments of compounds as described above, X is S.

In some preferred embodiments of compounds as described above, Y is O. In other preferred embodiments of compounds as described above, Y is S.

In some preferred embodiments of compounds as described above, $R_1$ is H or alkyl. In some preferred embodiments of compounds as described above, $R_2$ and/or $R_3$ is H or alkyl.

In preferred embodiments of compounds as described above, $R_2$ is selected from the group consisting of:

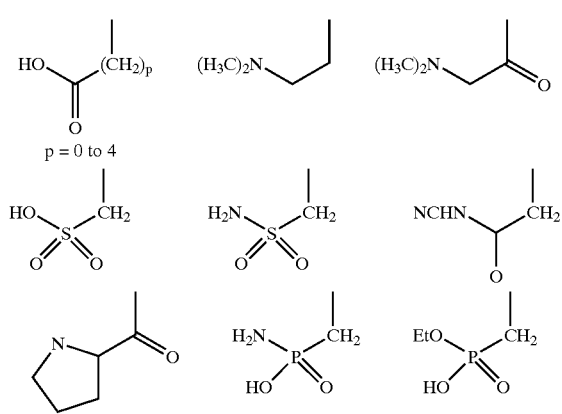

Active compounds of the present invention may be produced by the procedures described herein, or variations thereof which will be apparent to those skilled in the art. Novel intermediates useful for producing the active compounds described herein are also an aspect of the present invention, as are novel methods useful for producing such intermediates and active compounds.

B. Formulations and Pharmaceutically Acceptable Salts.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy, which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Fomrulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

C. Methods of Use.

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

The unusual profile of FAA and its unclear mode of action make the development of structural analogs of great interest. Accordingly, we designed, synthesized and evaluated a series of 2-phenyl-4-quinolone acetic acids, with an acetic acid side chain at different positions of the A ring. These compounds combine the skeleton of the 2-phenyl-4-quinolones with the acetic acid side chain of FAA. 2-Phenyl-4-quinolone-8-acetic acid also is a bioisostere of FAA; NH replaces the O in the pyrone ring.

Scheme 2

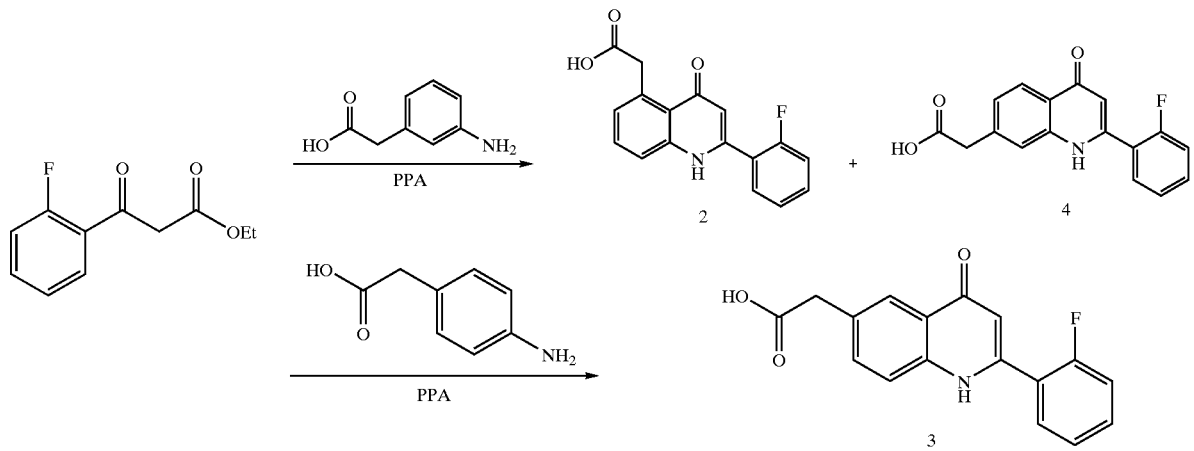

Scheme 2 shows the preparation of 2-phenyl-4-quinolone 5-, 6-, and 7-acetic acids. The 6-acetic acid (3) was efficiently prepared by condensation of commercially available 4-aminophenylacetic acid and ethyl 2'-fluorobenzoylacetate when heated (90–100° C.) in polyphosphoric acid (PPA) for 2.5 h. The 5-acetic acid (2) and the 7-acetic acid (4) were obtained by condensation of 3-aminophenyl acetic 10 acid and ethyl 2-fluorobenzoylacetate in PPA; the two isomers were separated by column chromatography.

As shown in Scheme 2, the unsubstituted and 2-(2'-fluorophenyl)-4-quinolone-8-acetic acids (11, 12) were prepared from the key intermediate, methyl 2-aminophenylacetate (6), and ethyl benzoylacetate (7) and ethyl 2-fluorobenzoylacetate (8).

Scheme 2

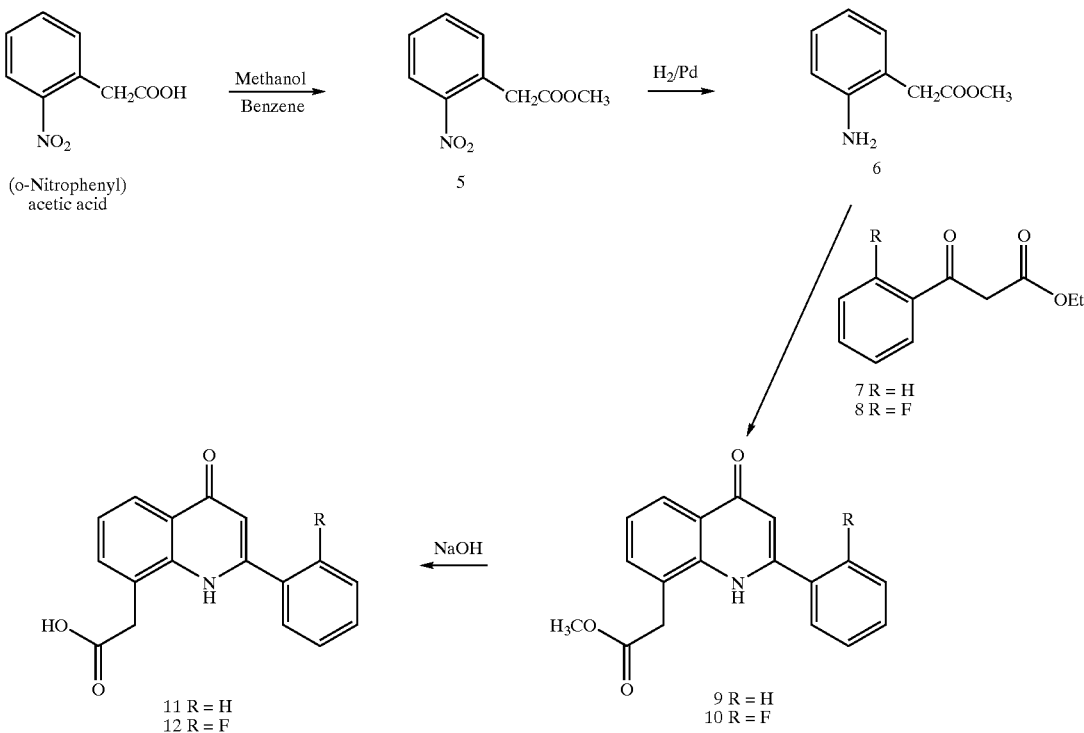

Compound 6 was synthesized by esterification of commercially available (o-nitrophenyl)acetic acid followed by reduction of the nitro group. However, 6 readily undergoes an intramolecular cyclization to the 2-oxindole via neutral and base catalyzed proton transfer (T. Fife and N. Duddy, *J. Amer. Chem. Soc.* 1983, 105, 74). Therefore, it was freshly made and condensed immediately with ethyl benzoylacetates 7 and 8, to give esters 9 and 10, which then were hydrolyzed with aq. NaOH to the corresponding acids 11 and 12.

General Procedure for the Synthesis of 2-Phenyl-4-quinolone Acetic Acids and Their Esters. Methyl 2-aminophenylacetate (6) (1.65 g, 10 mmol) was suspended in 8 g of polyphosphoric acid (PPA). The mixture was warmed at 90–100° C., and 1.92 g (10 mmol) of ethyl benzoylacetate (7) was added dropwise. The resulting mixture was further stirred for 1 h. After cooling, water was added, then aqueous NaOH (10%) was added slowly until pH=6 and the solution extracted with CHCl$_3$. The organic layer was dried over sodium sulfate and concentrated in vacuo. Chromatography using CHCl$_3$/CH$_3$OH (30:1) as eluant afforded 2.93 g of compound 9, yield 65.5%; mp 76–78° C.; $^1$H NMR (CDCl$_3$) δ 3.77 (s, 3H, CH$_3$), 3.95 (s, 2H, CH$_2$), 6.65 (s, 1H, H-3), 7.28 (m, 2H, H-6, H-7), 7.56 (m, 3H, H-3', H-4', and H-5'), 7.82 (m, 2H, H-2', H-6'), 8.34 (d, 1H, J=8.0Hz, H-5).

2-Phenyl-4-quinolone-8-acetic acid (11). 2-Phenyl-4-quinolone-8-methyl acetate (9) (150 mg, 0.51 mmol) was suspended in 50% aqueous EtOH (10 mL) containing NaOH (100 mg). The mixture was heated under reflux for 2 h. After cooling, the solution was slowly acidified with aqueous HCl. The precipitate was collected, and washed with water to provide 140 mg of 11, yield 98%; mp 238–240° C.; $^1$H NMR (DMSO-d$_6$) 67 4.17 (s, 2H, CH$_2$), 7.40 (s, 1H, H-3), 7.56 (m, 2H, H-6, H-7), 7.61–8.01 (m, 5H, aromatic), 8.14 (d, 1H, H-5).

2-(2'-Fluorophenyl)-4-quinolone-8-acetic acid (12). Obtained by hydrolysis of 10 with aqueous 50% EtOH containing NaOH using the same synthetic procedure as for 11, yield 78.9 %; mp 243–245° C.; $^1$H NMR (DMSO-d$_6$) δ 4.07 (s, 2H, CH$_2$), 7.35 (s, 1H, H-3), 7.35–7.40 (m, 4H, H-6, H-7, H-3' and H-5'), 7.53–7.63 (m, 2H, H-4', H-6'), 8.08 (dd, 1H, J=3.7, 9.0Hz, H-5), 12.0 (br s, 1H, NH).

Compounds 2–4 and 9–12 were evaluated in a tubulin polymerization assay and for cytotoxicity. Tubulin polymerization assays were performed as described in Y. Xia et al., *J. Med. Chem.* 1998, 41, 1155. Cytotoxic assays were performed as described in L. Rubinstein et al., *J. Natl. Cancer Inst.* 1990, 82, 1113–8.

As shown in Table 1, the 5-(2), 7-(4), and 8- (11) acetic acid compounds were totally inactive in this tubulin polymerization assay, however, the 6-substituted compound (3) showed an increased activity. The methyl ester (9) and 2'-fluoro analog (12) of 11 also were inactive (IC$_{50}$>40 μM), while compound 10, which contained both functionalities, was about 4-fold more active. Compounds 2–4 and 9–10 displayed moderate cytotoxicity in vitro against seven human tumor cell lines, including epidermoid, bone, ovarian, glioblastoma, melanoma, lung, and breast cancer cell lines. Among these five compounds, 10, the most potent compound in the tubulin assay, was more active than the 5-, 6-, or 7-acetic acid quinolones. In addition, 10 showed selective activity against ovarian cancers. Interestingly, 2-phenyl-4-quinolone-8-acetic acid (11) and 2-(2'-fluorophenyl)-4-quinolone-8-acetic acid (12), which were inactive in the tubulin assay, were extremely potent in the cytotoxic assay. The ED$_{50}$ values of these two compounds were less than 0.1 μg/mL against most tested cell lines. Therefore, a new mechanism or target might be involved instead of tubulin.

TABLE 1

Biological Activities of 2-Phenyl-4-quinolone Acetic Acids and Their Esters

| | ED$_{50}$ (μg/mL)[a] | | | | | | | ITP[c] IC$_{50}$ |
|---|---|---|---|---|---|---|---|---|
| | KB[b] | HOS[b] | 1A9[b] | U87-MG[b] | SKMEL-2[b] | A549[b] | MCF-7[b] | (μM) |
| 2 | NA | NA | NA | NA | >20(9) | >20(8) | >20(7) | >40 |
| 3 | >20(36) | >20(15) | >20(37) | >20(9) | >20(17) | >20(24) | >20(16) | 10–20 |
| 4 | >20(8) | NA | >20(15) | NA | >20(14) | >20(21) | >20(13) | 20–40 |
| 9 | >20(8) | >20(7) | >20(30) | NA | >20(12) | NA | >20(15) | >40 |
| 10 | >10(29) | >10(18) | 7.50 | NA | >10(11) | >10(22) | >10(14) | ~10 |
| 11 | 0.04 | 0.07 | 0.04 | 0.12 | 0.06 | 0.11 | 0.44 | >40 |
| 12 | 0.03 | 0.04 | 0.02 | 0.07 | 0.05 | 0.06 | 0.12 | >40 |

[a]Cytotoxicity, ED$_{50}$ for each cell line, is the concentration of compound that causes a 50% reduction in adsorbance at 562 nm relative to untreated cells using the SRB assay (see, e.g., Y. Xia et al., J. Med. Chem 41, 1155 (1998).
[b]Cell lines include human epidermoid carcinoma of the nasopharynx (KB), bone carcinoma (HOS), human ovarian cancer (1A9), glioblastoma carcinoma (U-87-MG), human melanoma cancer (SKMEL-2), human lung cancer (A549), and human breast cancer (MCF-7).
[c]Tubulin polymerization was evaluated as described above. A minimum of two independent experiments was performed with each compound. The IC$_{50}$ value is defined as the concentration that inhibits the extent of assembly by 50% after 20 min at 30° C.

In summary, these findings with the 2-phenyl-4-quinolone acetic acid derivatives showed unique and interesting results. 2-Phenyl-4-quinolone-8-acetic acid and 2-(2'-fluorophenyl)-4-quinolone-8-acetic acid are the most structurally similar to FAA and were only the highly active antitumor compounds in this series. Unlike most 2-phenyl-4-quinolones, they were not inhibitors of tubulin polymerization. 2-Phenyl-4-quinolone-6-acetic acid (3) showed slight inhibition of tubulin polymerization.

The foregoing is illustrative of the present invention, and is not to be construed as limiting thereof. The invention is defined by the following claims, with equivalents of the claims to be included therein.

What is claimed is:

1. A compound having a structure according to Formula I:

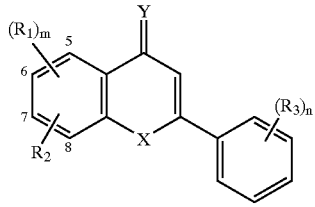

wherein:
X is selected from the group consisting of O and S;
Y is selected from the group consisting of O and S;
m is from 1 to 3;
n is from 1 to 5;
$R_1$ and $R_3$ are each independently selected from the group consisting of H, hydroxy, lower alkyl, lower alkoxy, halo, amino, aminoalkyl, nitro, heteroaryl, —OC(=O)$R_6$, —O(C=O)O$R_6$; and —O(C=O)N($R_6$)$_2$;
subject to the proviso that at least one of $R_1$ and $R_3$ is not H;
$R_2$ is selected from the group consisting of:

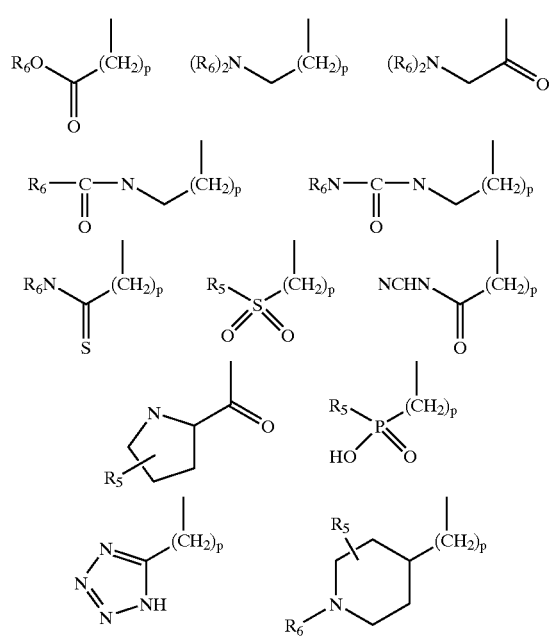

where p is 0 to 4, $R_5$ is hydroxy, alkoxy or amino, and $R_6$ is H or lower alkyl;
or a pharmaceutically acceptable salt thereof.

2. A compound according to claim 1 having a structure according to Formula I, and wherein $R_2$ is bonded at the 8 position.

3. A compound according to claim 1 wherein X is O.

4. A compound according to claim 1 wherein X is S.

5. A compound according to claim 1 wherein Y is O.

6. A compound according to claim 1 wherein Y is S.

7. A compound according to claim 1 wherein $R_1$ is H or alkyl.

8. A compound according to claim 1 wherein $R_3$ is H or alkyl.

9. A compound according to claim 1 wherein $R_2$ is selected from the group consisting of:

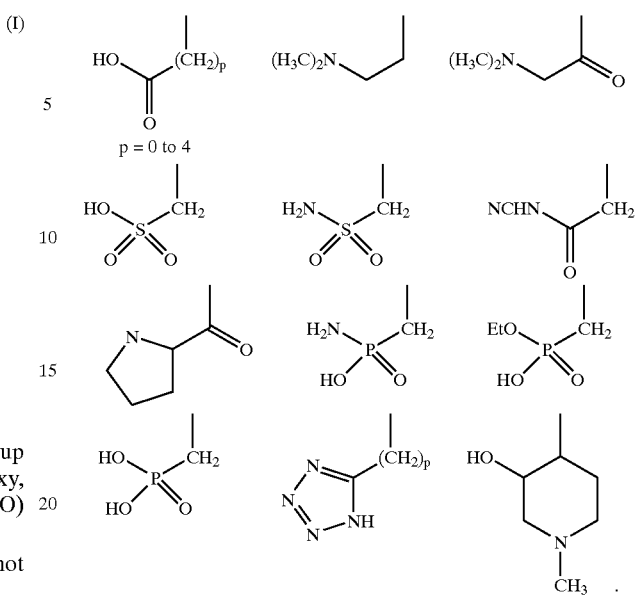

10. A pharmaceutical formulation comprising a compound according to claim 1 in a pharmaceutically acceptable carrier.

11. The pharmaceutical formulation according to claim 10, wherein said carrier is an aqueous carrier.

12. A method of treating a cancer, comprising administering to a subject in need thereof a treatment effective amount of a compound according to claim 1, or a pharmaceutically acceptable salt thereof.

13. The method according to claim 12, wherein said cancer is selected from the group consisting of skin cancer, lung cancer, Kaposi's sarcoma, testicular cancer, lymphoma, leukemia, esophageal cancer, stomach cancer, colon cancer, breast cancer, endometrial cancer, ovarian cancer, central nervous system cancer, liver cancer and prostate cancer.

14. The method according to claim 12, wherein said cancer is prostate cancer.

15. The method according to claim 12, wherein said cancer is colon cancer.

16. The method according to claim 12, wherein said cancer is lung cancer.

17. The method according to claim 12, wherein said cancer is breast cancer.

18. The method according to claim 1 wherein $R_2$ is selected from the group consisting of:

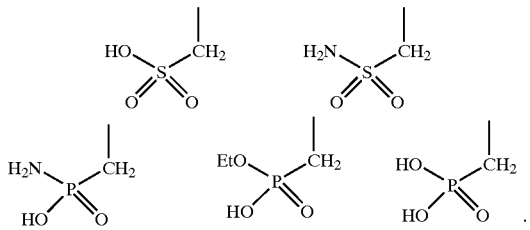

19. A compound according to claim 1 wherein $R_2$ is selected from the group consisting of:

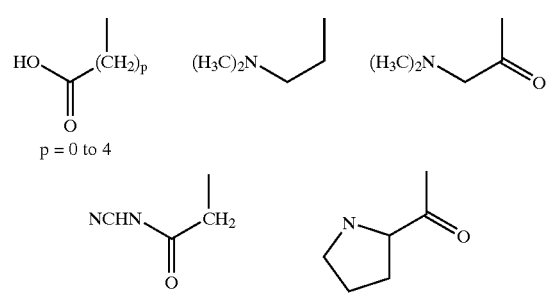
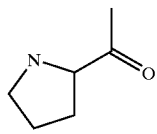
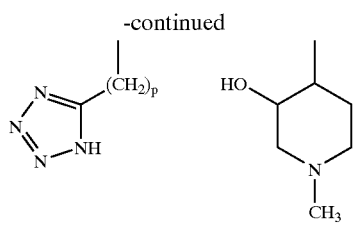
* * * * *